United States Patent
Huang (10) Patent No.: US 9,370,596 B2
(45) Date of Patent: Jun. 21, 2016

(54) FAN DEVICE WITH AIR GUIDE FUNCTION

(75) Inventor: Shu Li Huang, Taipei (TW)

(73) Assignee: BEL'AIR INTERNATIONAL GROUP LTD., Taipei (TW)

( * ) Notice: Subject to any disclaimer, the term of this patent is extended or adjusted under 35 U.S.C. 154(b) by 1013 days.

(21) Appl. No.: 13/528,570

(22) Filed: Jun. 20, 2012

(65) Prior Publication Data
US 2013/0340867 A1    Dec. 26, 2013

(51) Int. Cl.
*A61L 9/12* (2006.01)
*F04D 25/08* (2006.01)
*F04D 29/54* (2006.01)
*B05B 7/00* (2006.01)

(52) U.S. Cl.
CPC ............. *A61L 9/122* (2013.01); *F04D 25/08* (2013.01); *F04D 29/547* (2013.01); *B05B 7/0081* (2013.01); *Y10T 137/85978* (2015.04)

(58) Field of Classification Search
CPC ..... F04D 19/002; F04D 25/105; F04D 29/18; F04D 29/181; F04D 29/547; F04D 29/542; F04D 29/544; F04D 29/703; F04D 29/705; F04D 29/545; F04D 29/002; F04D 29/005; F05D 2240/126; A61L 9/00; A61L 9/15; A61L 9/04; A61L 9/122
See application file for complete search history.

(56) References Cited

U.S. PATENT DOCUMENTS

| | | | | |
|---|---|---|---|---|
| 1,034,777 | A * | 8/1912 | Foster | 422/124 |
| 1,091,929 | A * | 3/1914 | Hammesfahr | 422/124 |
| 1,308,845 | A * | 7/1919 | Flanders | 422/124 |
| 1,323,462 | A * | 12/1919 | Flanders | 422/124 |
| 1,439,881 | A * | 12/1922 | Fontaine | 422/124 |
| 4,084,491 | A * | 4/1978 | Spotts et al. | 454/285 |
| 4,521,153 | A * | 6/1985 | Morimoto et al. | 415/146 |
| 5,970,643 | A * | 10/1999 | Gawel, Jr. | 43/1 |
| 2009/0317240 | A1* | 12/2009 | Wei | 415/127 |
| 2010/0003126 | A1* | 1/2010 | Wang | 415/146 |
| 2010/0303617 | A1* | 12/2010 | Chen | 415/208.2 |

* cited by examiner

*Primary Examiner* — Dwayne J White
*Assistant Examiner* — Danielle M Christensen
(74) *Attorney, Agent, or Firm* — Rabin & Berdo, P.C.

(57) ABSTRACT

A fan device with air guide function, which contains at least a fan device and is characterized by comprising an air guide frame, wherein the said air guide frame is composed of at least two layers inclined guide which are configured as a symmetrical geometrical shape or at least two layers of arc-overlapped inclined guide which forms a arc-overlapped air guide frame, and are both connected by the securing elements. By the combination of the fan device and both embodiments of the air frame guide, the present invention is applicable to guide the air flow propelled from the fan with a prolonged air path in the space and provides higher air molecule freedom by the effect of more frequent collision which results each loose air molecule has larger surface area existing and moving in the air flow, enables a better indoor air circulation and forms comfortable and nature breeze.

15 Claims, 12 Drawing Sheets

FAN DEVICE WITH AIR GUIDE FUNCTION

BACKGROUND OF THE INVENTION

1. Field of the Invention

The present invention is related to a fan device with air guide function, wherein the fan device is configured with an air guide frame which provides each air molecule with higher space freedom and surface area existing in the space by more frequent collision. Thus, after propelling from the fan and colliding with the air guide frame, the air flow becomes more comfortable and feels like a nature breeze when it touches human skin, and the present invention is applicable in all types of electric fan or any structure blowing the air.

2. Description of Related Art

Traditionally, an electric fan is always driven by the inner motor to blow the air forward and is equipped with a protection frame to avoid touching with the rotating fan. Therefore, that electric fan only functions as a device to pump the air forward. The said protection frame is also linked with a reducing gear to make it rotatable and the air flows like a swirl.

However, the air is flowing strong at the front only and could not provide a better circulation effect around the whole indoor space. Furthermore, the prior electric fan might not be able to make an indoor space full of a fresh and fragrant air or its air flow is still too strong to produce an air like natural breeze. Even the prior electric fan is equipped with a swing gear to control the electric fan swinging to and fro with certain angle coverage, there is still a limited space for circulation.

In view of these drawbacks and problems, the present invention aims to provide a fan device with air guide function that is applicable to an existed air blowing device to convert an air flow generated therefore into a mild and comfortable flow of air that similar to a natural breeze with an aromatic essence or perfume for indoor air refreshing purpose.

SUMMARY OF THE INVENTION

The primary objective of the present invention is to provide a fan device with air guide function, which comprises at least a fan device and is characterized by comprising an air guide frame, wherein the said air guide frame is configured at the front of the said fan device and is composed of at least two layers inclined guide which are configured as a symmetrical geometrical shape and are connected by the securing elements. By the combination of the fan device and the air frame guide, the present invention is applicable to guide the air flow propelled from the fan with a prolonged air path in the space and provides higher air molecule freedom by the effect of more frequent collision which results loose air molecule has larger surface area existing in the air flow, enables a better indoor air circulation and forms a mild and comfortable breeze.

The second objective of the present invention is to provide a fan device with air guide function, which comprises at least a fan device and is characterized by comprising an arc-overlapped air guide frame, wherein the said air guide frame is configured at the front side of the fan device and is composed of at least two layers of arc-overlapped inclined guide which are configured by a plural of arc sections overlapped to form each arc-overlapped inclined guide which is configured as a one-piece symmetrical geometrical structure with equal separation and is connected by the securing elements.

The third objective of the present invention is to provide a center rod which is equipped at the mid of air guide frame and is configured with a round groove near the front end of the center rod to have the essential oil bottle hung on the round groove. The center rod can be fixed with the fan device or the air guide frame. Therefore, the guided flow of air molecule is able to mix with the essence of the oil bottle and provides a pleasing indoor circulation function with air refreshing and comfortable breeze.

Another objective of the present invention is to provide a fan device with air guide function, wherein the fan device could be selected from any one of the table electric fans, high-standing electric fans, box electric fans or circulation fans set. Especially, the twin circulation fans set and the triple circulation fans set provides more application of the main purpose related to the present invention. Therefore, they broaden the coverage, application and practical function of the present invention.

To achieve the said objectives, the present invention provides a fan device with air guide function, which contains at least a fan device and is characterized by comprising an air guide frame, wherein the said air guide frame is composed of at least two layers inclined guide or at least two layers of arc-overlapped inclined guide which is configured by a plural of overlapped arc sections, and both embodiments of air guide frame are formed as a one-piece symmetrical geometrical structure with securing elements connected between each layer inclined guide.

Therefore, the present invention is applicable to enable a combination of the existing fan device with the air guide frame respectively to generate a mild and comfortable breeze and to perform a better indoor air refreshing with some aromatic essence or perfume located inside the oil bottle.

The function and structure of practical embodiments can be further understood via the drawings listed below.

BRIEF DESCRIPTION OF THE DRAWINGS

The present invention can be further understood from the following drawings.

DETAILED DESCRIPTION OF THE PREFERRED EMBODIMENTS

With reference to the FIGS. from 1 to 12, the present invention relates to a fan device with air guide function, which comprises at least a fan device 10 and is characterized by comprising an air guide frame 20, wherein the said air guide frame 20 is configured at the front of the said fan device 10 and is composed of at least two layers inclined guide 21 which are configured as a symmetrical geometrical shape and are connected by the securing elements 22. By this combination of the fan device 10 and the air frame guide 20, the present invention guides the air flow propelled from the fan with a prolonged air path in the space and provides higher air molecule freedom by the effect of more frequent collision which results loose air molecule has larger surface area existing in the air flow, enables a better indoor air circulation and forms a mild and comfortable breeze.

Another embodiment of the present invention also comprises at least a fan device 10 and is characterized by comprising an arc-overlapped air guide frame 25, wherein the said air guide frame 25 is configured at the front side of the fan device 10 and is composed of at least two layers of arc-overlapped inclined guide 24 which are configured by a plural of arc sections overlapped to form each arc-overlapped inclined guide 24 which is formed as a one-piece symmetrical geometrical structure and is connected by the securing elements 22 with equal distance between each arc-overlapped inclined guide 24.

Figure 1:
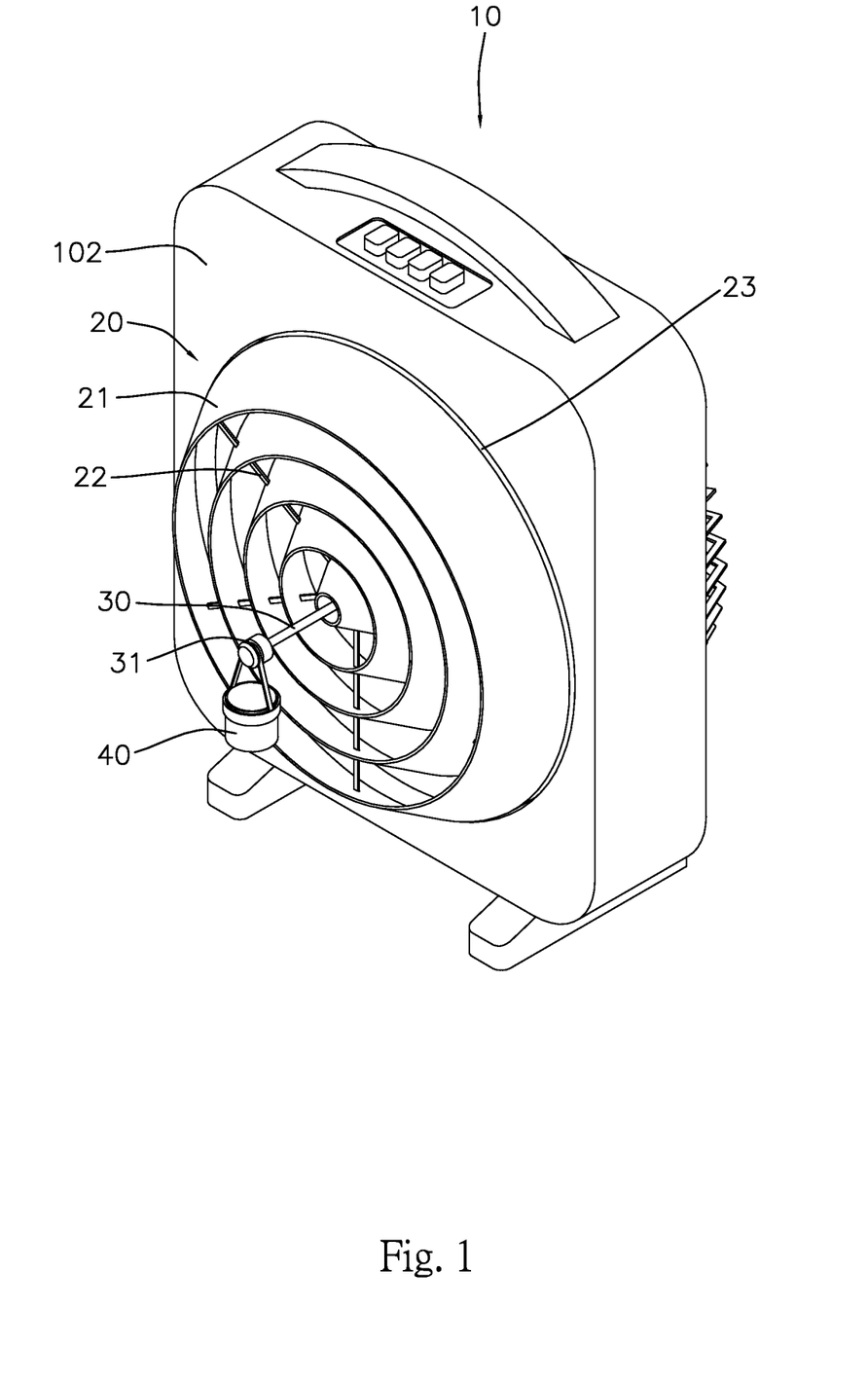
FIG. 1 is a perspective view of the present invention.
Figure 2:
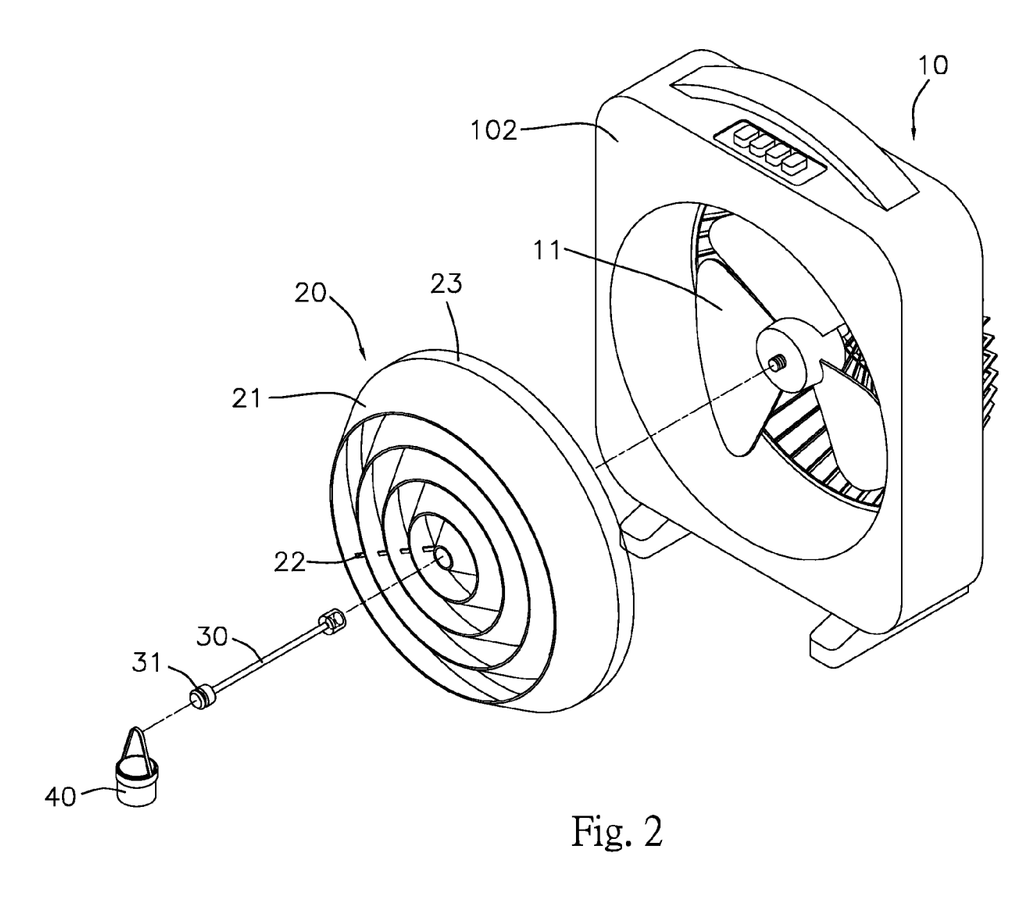
FIG. 2 is an element decomposition view of the present invention.
Figure 3:
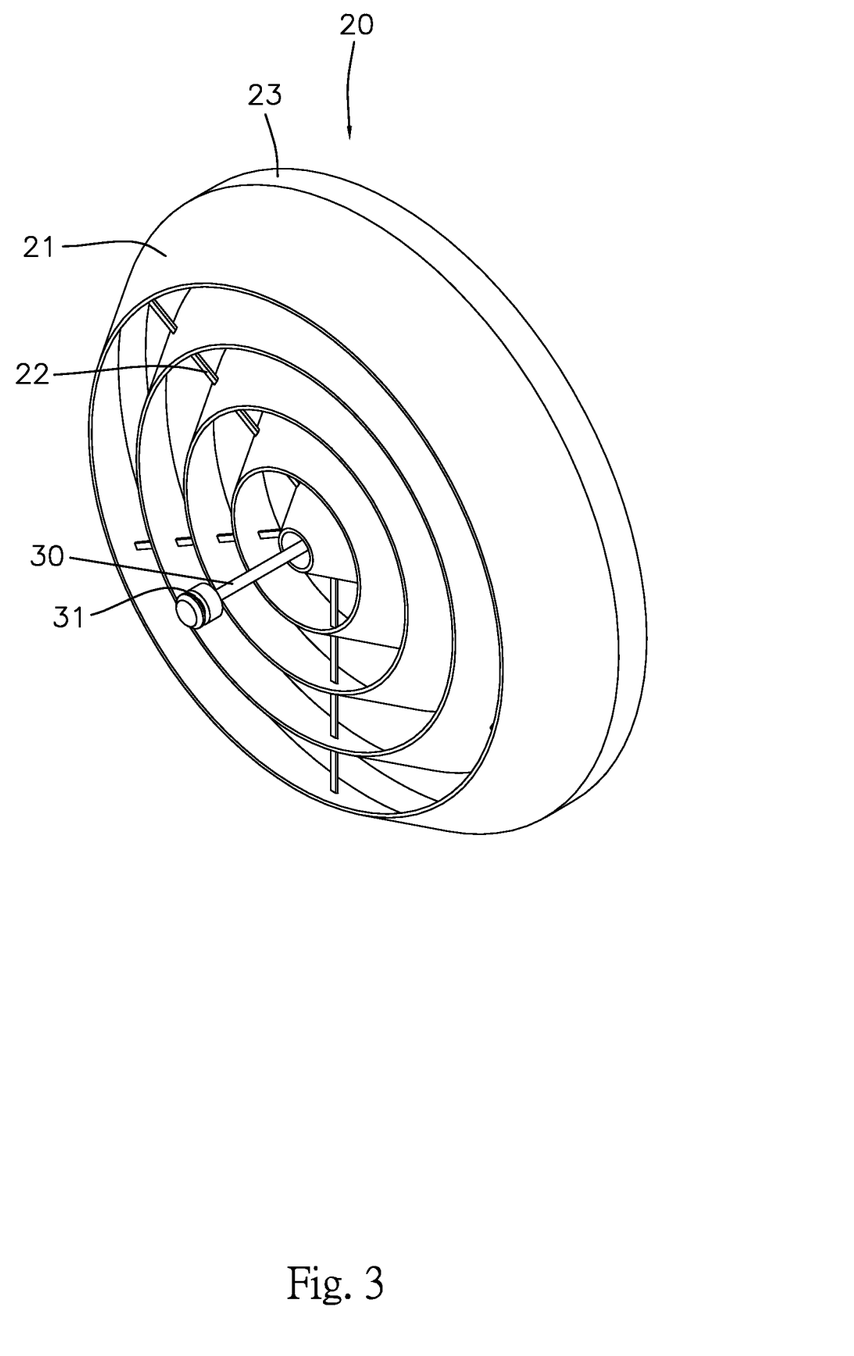
FIG. 3 is a schematic view of the air guide frame.
Figure 4:
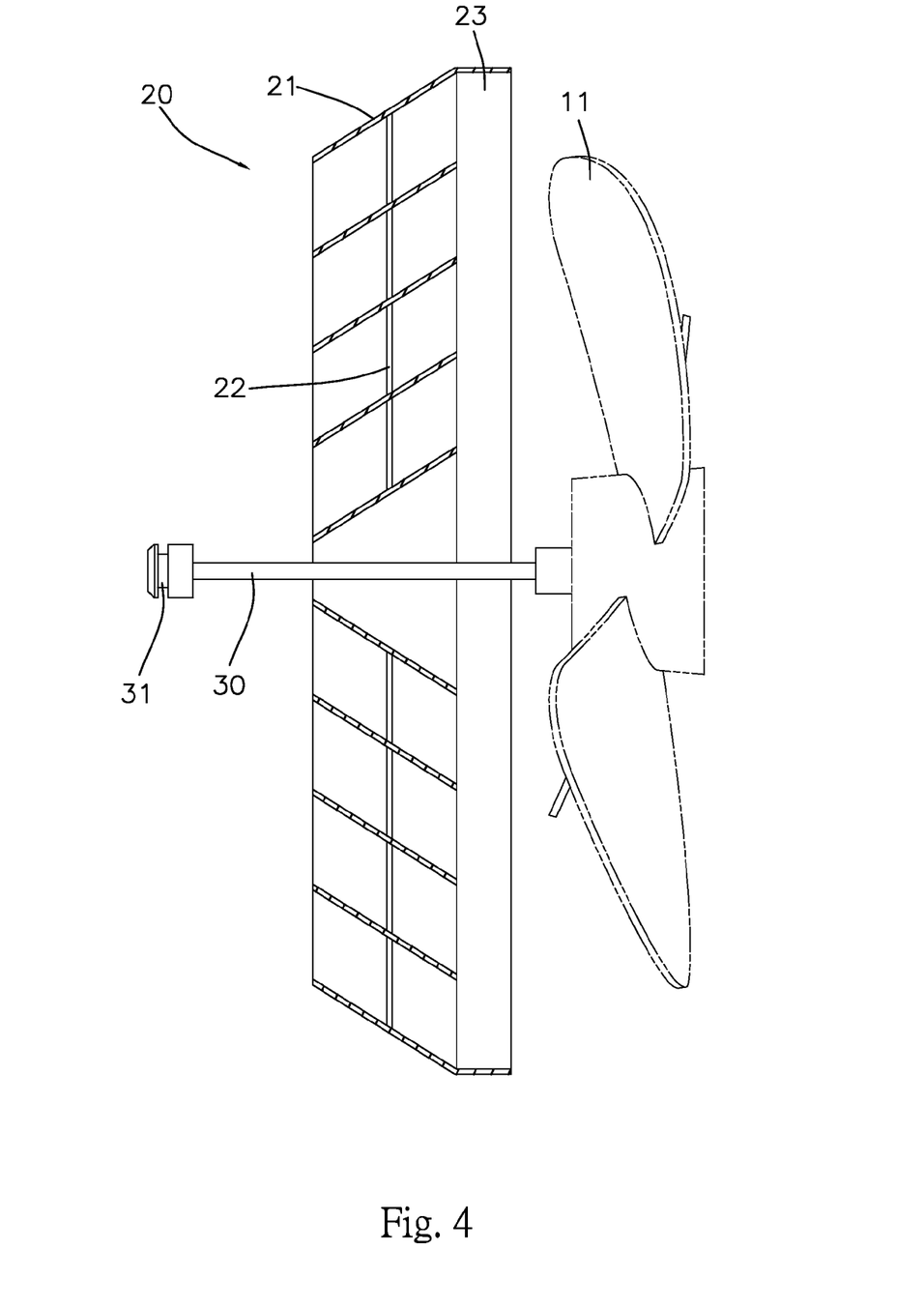
FIG. 4 is a schematic cross-section view of the air guide frame.
Figure 5:
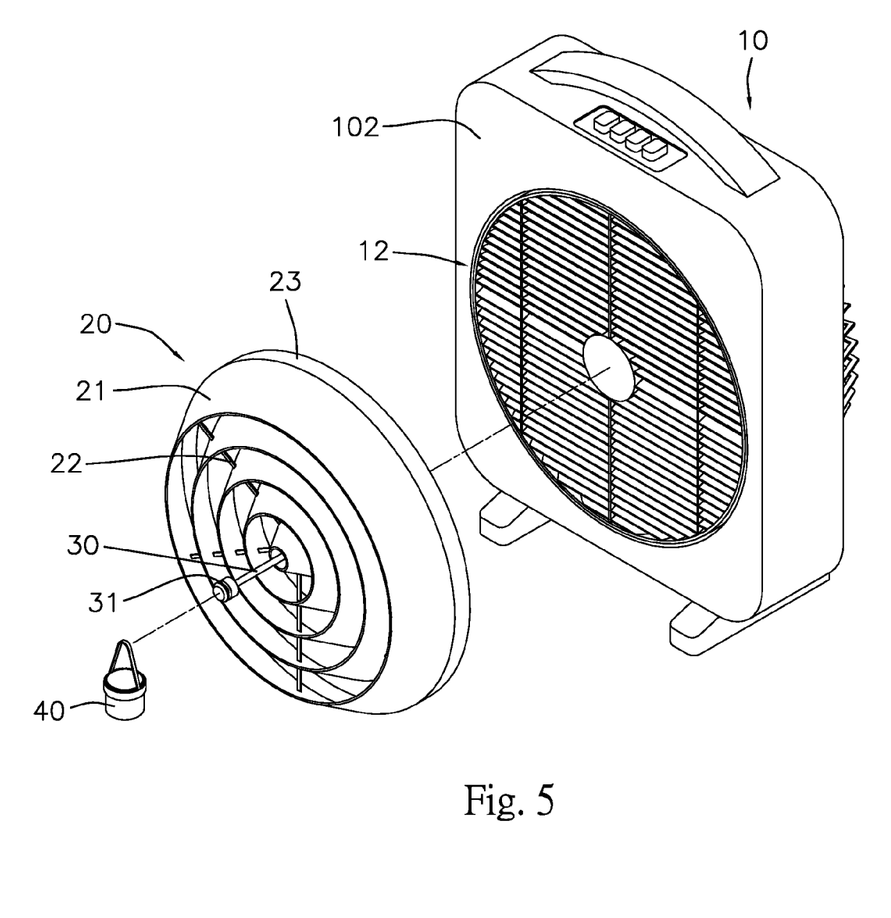
FIG. 5 is an element decomposition view of the second embodiment of the present invention.
Figure 6:
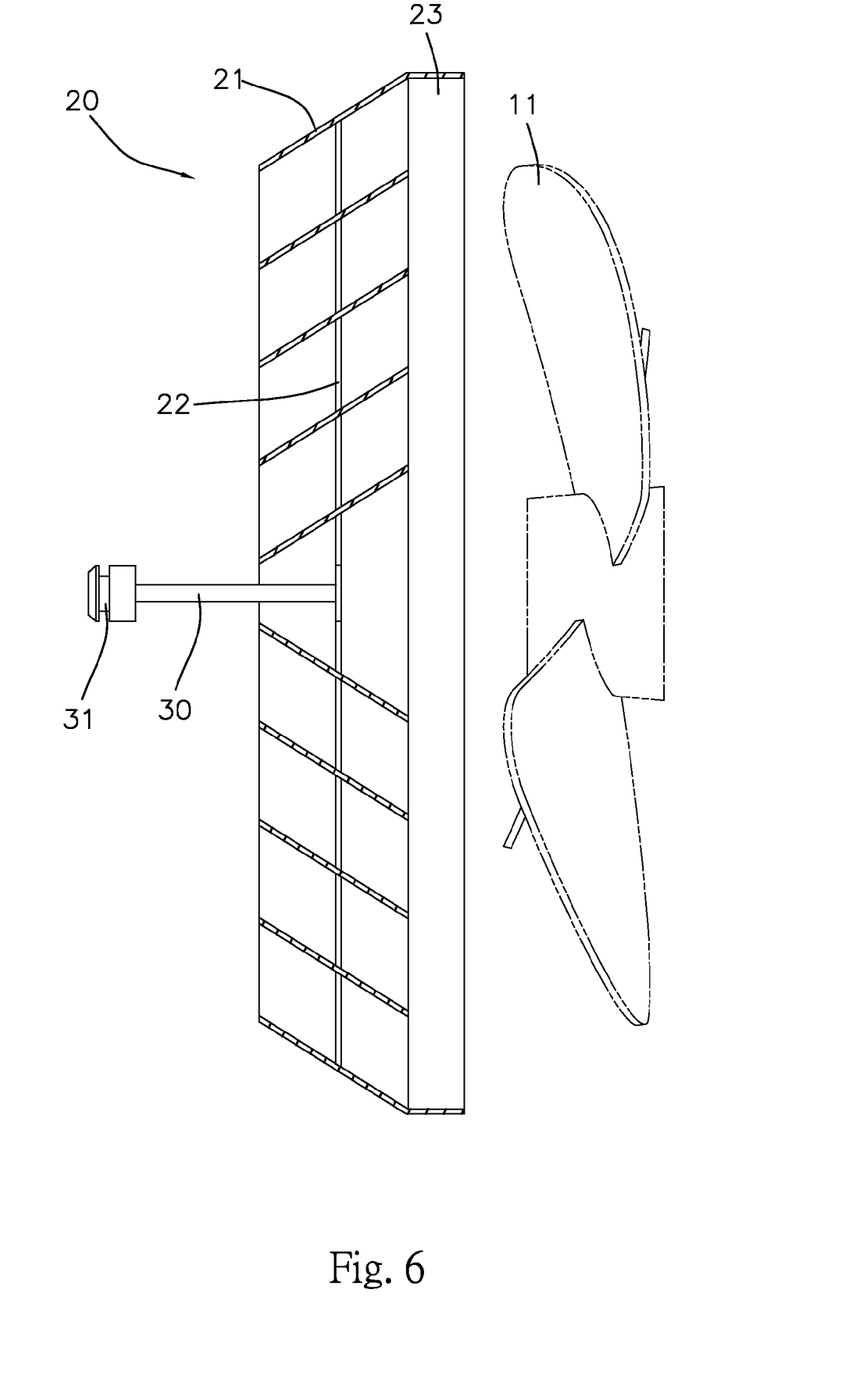
FIG. 6 is a schematic cross-section view of the air guide frame illustrating the second embodiment.
Figure 7:
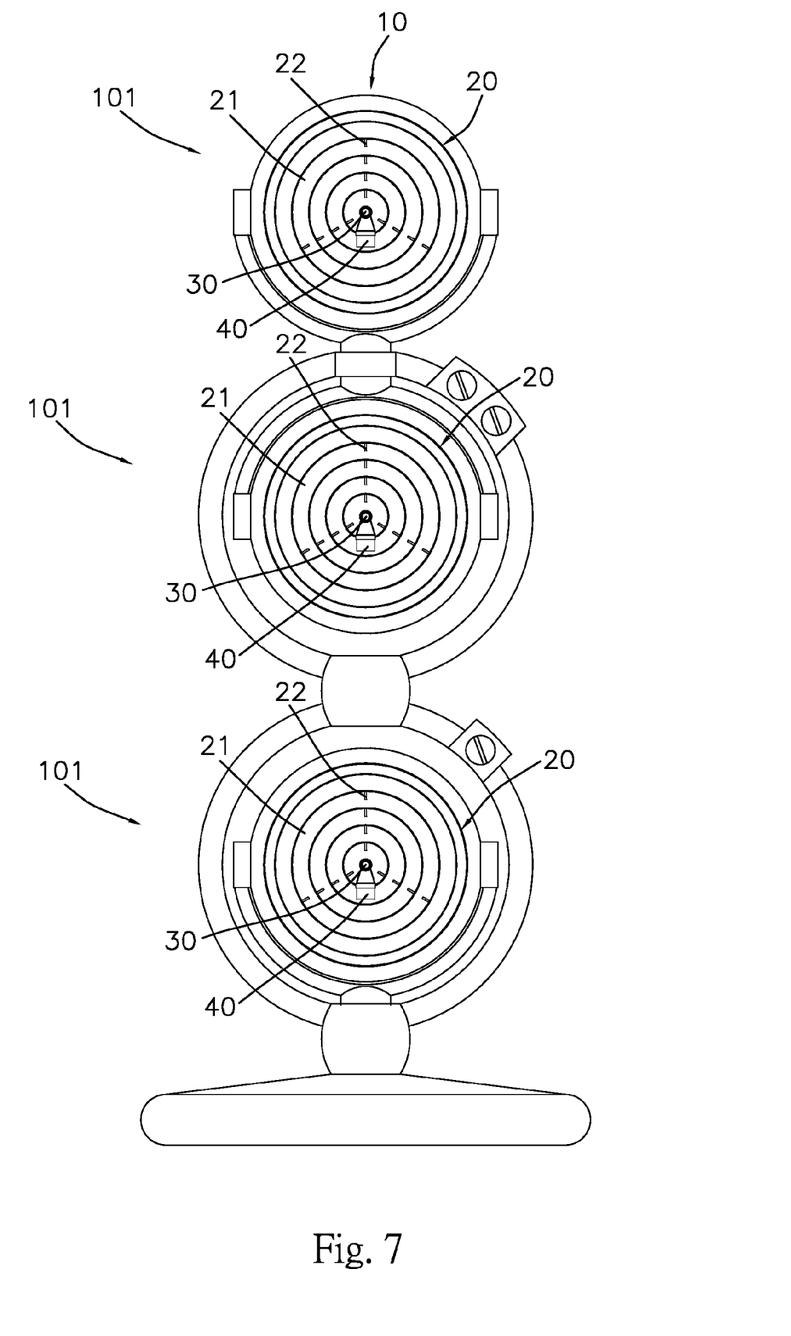
FIG. 7 is a perspective view of circulation fan set according to the second embodiment of the present invention.
Figure 8:
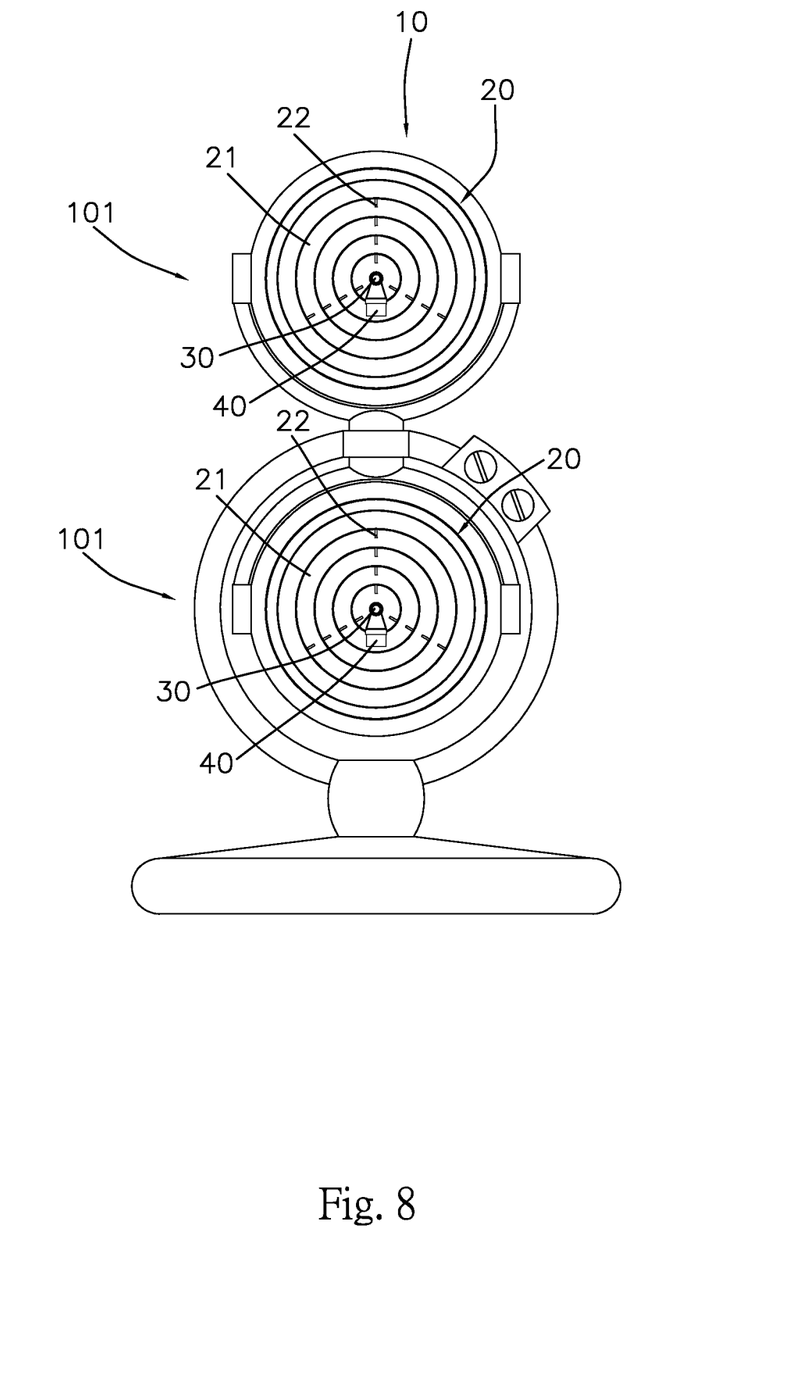
FIG. 8 is another perspective view of circulation fan set related to the second embodiment.
Figure 12:
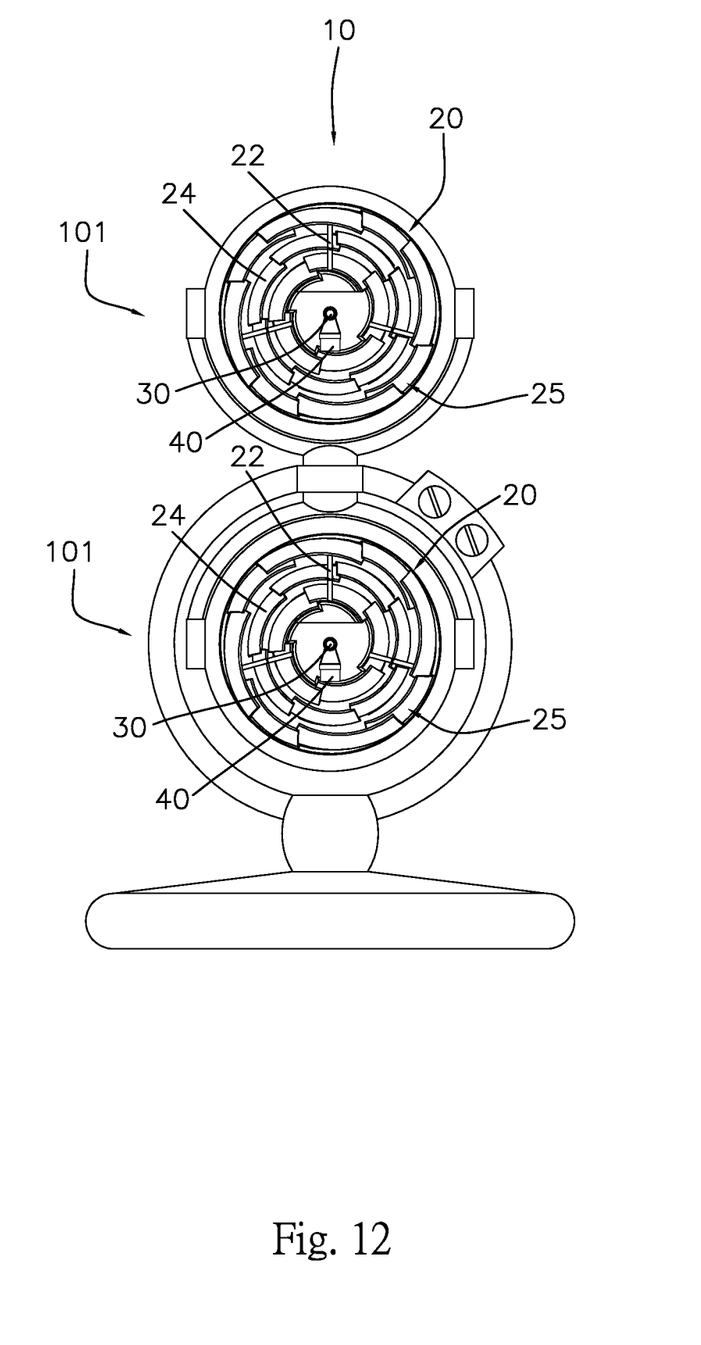
FIG. 12 is a perspective view of circulation fan set related to the third embodiment

Meanwhile, the front of fan device 10 is further equipped with a protection frame 12 and the air guide frame 20 can be assembled with the protection frame 12 by the fitting edge 23 at the rim position and can rotate synchronously. And, there is a center rod 30 configured at the mid of the air guide frame 20 to have an assembly with the fan device 10. The front end of the center rod 30 is formed with a round groove 31 to hang the essence oil bottle 40. Thus, the air flow propelled from the fan can mix the essence molecule providing a pleasing air circulation and comfortable breeze. The multi layers air guide frame 20 could be constructed as a form of round or square symmetrical geometrical shape with a fitting edge 23 to joint with different size of those prior electric fans. Besides, the fan device 10 can be a circulation fan set 101 which chooses from the twin or triple circulation fans set (as shown in FIG. 7, 8 or 12).

Please refer to the FIGS. from 1 to 12, the present invention is characterized by comprising an air guide frame 20 which is configured at the front of the said fan device 10 and is composed of at least two layers inclined guide 21 which are configured as a symmetrical round or square shape and are connected by the securing elements 22 to form the structure of air guide frame 20. As the air comes out from protection frame 12, the air molecule collides with each other along a prolonged path and it provides the molecule has more spreading ability and had better indoor air circulation after the mixture of air flow and the essence inside oil bottle. When both molecules become loose mixture with more surface area and spread over the indoor space, the present invention generates a mild and comfortable breeze and performs an air refreshing with some aromatic essence or perfume.

Figure 9:
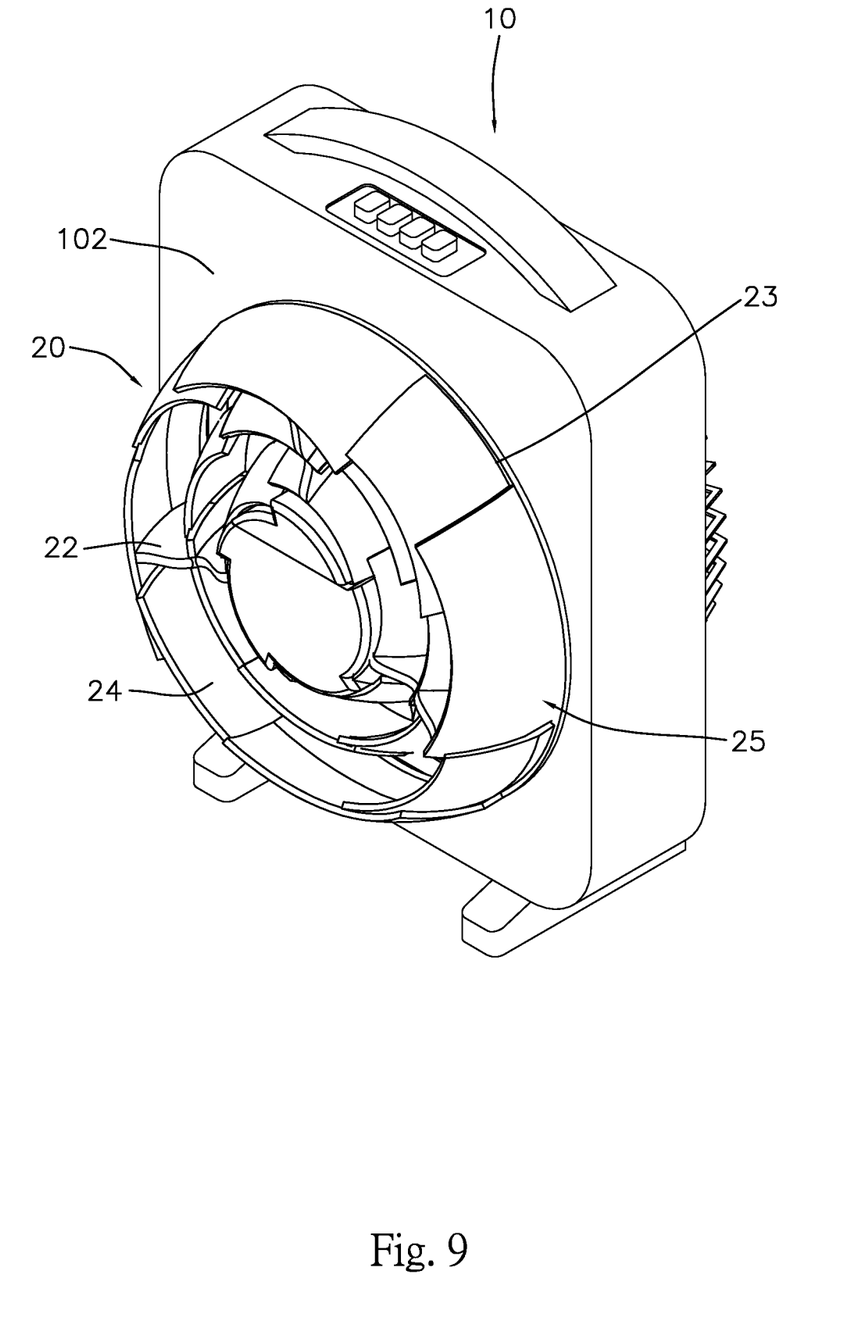
FIG. 9 is a perspective view of the third embodiment.
Figure 10:
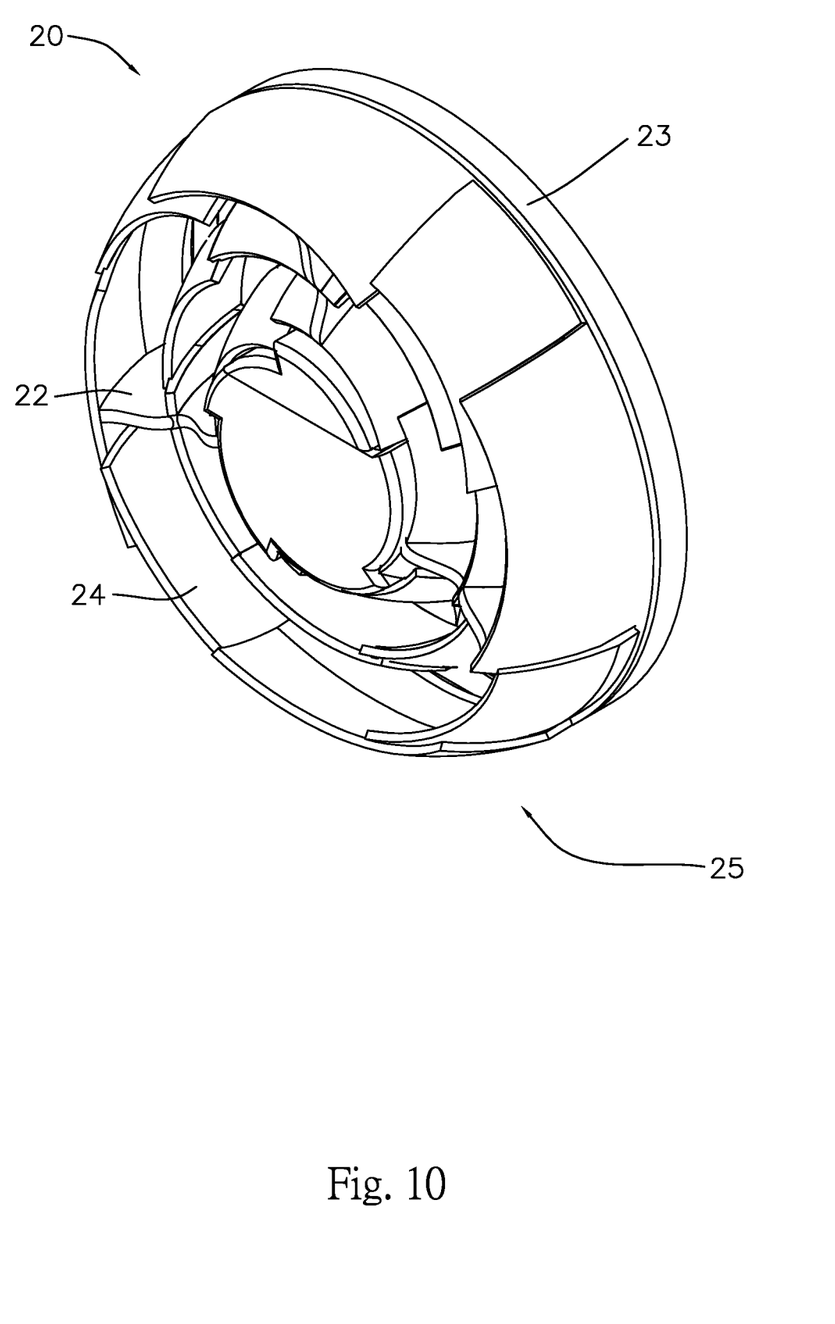
FIG. 10 is a perspective view of the arc-overlapped air guide frame according to the third embodiment.
Figure 11:
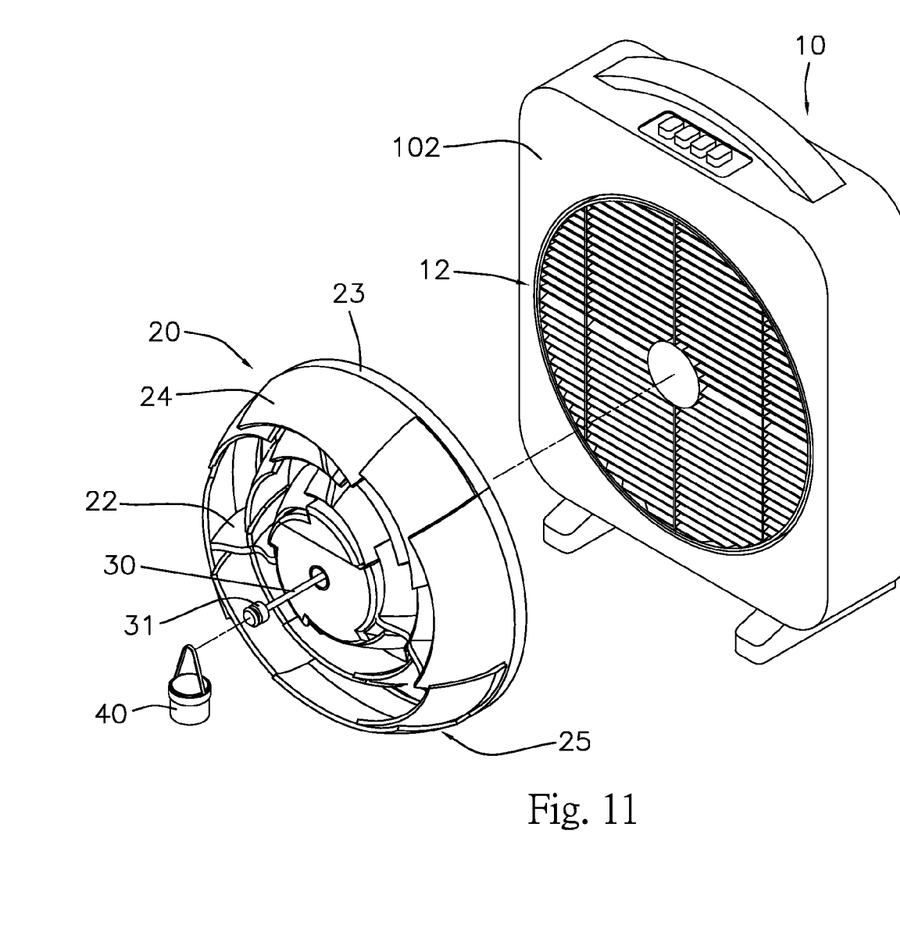
FIG. 11 is an element decomposition view related to the third embodiment.

Another embodiment (as shown in FIG. 9) of the present invention also comprises at least a fan device 10 and is characterized by comprising an arc-overlapped air guide frame 25 (as shown in FIG. 10), wherein the said air guide frame 25 is configured at the front side of the fan device 10 and is composed of at least two layers of arc-overlapped inclined guide 24 which are configured by a plural of arc sections overlapped to form each arc-overlapped inclined guide 24 which is formed as a one-piece symmetrical geometrical structure and is connected by the securing elements 22 with equal distance between each arc-overlapped inclined guide 24. Similarly, the front of fan device 10 is further equipped with a protection frame 12 and the arc-overlapped air guide frame 25 can be assembled with the protection frame 12 by the fitting edge 23 at the rim position and can rotate synchronously. And, there is a center rod 30 configured at the mid of the arc-overlapped air guide frame 25 (as shown in FIG. 11) to have an assembly with the fan device 10. The front end of the center rod 30 is formed with a round groove 31 to hang the essence oil bottle 40.

Of course, it is to be understood that the embodiments described herein are merely some illustrations related to the objects of the invention and that a wide variety of modifications thereto may be adopted without departing from the purpose and the scope of the present invention as set forth in the following claims.

What is claimed is:

1. A fan device with an air guide function, comprising:
a fan impeller;
an air guide frame positioned at a front side of the fan impeller, and having
at least two inclined guide layers configured as a round symmetrical geometrical shape, and
securing elements, said inclined guide layers being connected by the securing elements; and
a center rod positioned at a middle of the air guide frame and being connected to the fan impeller, the center rod having a round groove at a front end thereof, so that an essence oil bottle can be hung therefrom.

2. The fan device according to claim 1, further comprising a protection frame, and the air guide frame further having a fitting edge at a rim position thereof, and being assembled with the protection frame by the fitting edge, so that both rotate synchronously.

3. The fan device according to claim 1, wherein the air guide frame further has a fitting edge at a rim position thereof to join with the fan device.

4. The fan device according to claim 3, wherein the fan device is a circulation fan set.

5. The fan device according to claim 3, wherein the fan device is one of a table electric fan, high-standing electric fan, and box electric fan.

6. The fan device according to claim 1, wherein the fan device is a circulation fan set.

7. The fan device according to claim 1, wherein the fan device is one of a table electric fan, high-standing electric fan, and box electric fan.

8. A fan device with an air guide function, comprising:
a fan impeller; and
an arc-overlapped air guide frame, having
a plurality of securing elements, and
at least two arc-overlapped inclined guide layers constructed to have a round symmetrical geometrical shape, each layer having a plurality of overlapped arc sections, the layers each being a one-piece symmetrical geometrical structure, the layers having equal separation between each other and being connected by the securing elements.

9. The fan device according to claim 8, wherein the fan device further comprises a protection frame, and the arc-overlapped air guide frame further having a fitting edge at a rim position thereof, and being assembled with the protection frame by the fitting edge, so that both rotate synchronously.

10. The fan device according to claim 8, further comprising a center rod positioned at a middle of the arc-overlapped air guide frame and being connected with the fan device, the center rod having a round groove at a front end thereof, so that an essence oil bottle can be hung therefrom.

11. The fan device according to claim 8, wherein the arc-overlapped air guide frame further has a fitting edge at a rim position thereof to joint with the fan device.

12. The fan device according to claim 11, wherein the fan device is a circulation fan set.

13. The fan device according to claim 11, wherein the fan device is one of a table electric fan, high-standing electric fan, and box electric fan.

14. The fan device according to claim 8, wherein the fan device is a circulation fan set.

15. The fan device according to claim 8, wherein the fan device is one of a table electric fan, high-standing electric fan, and box electric fan.

\* \* \* \* \*